United States Patent [19]
Haskell

[11] 4,031,153
[45] June 21, 1977

[54] SEPARATION OF STYRENE FROM XYLENES

[75] Inventor: Donald M. Haskell, Bartlesville, Okla.

[73] Assignee: Phillips Petroleum Company, Bartlesville, Okla.

[22] Filed: Sept. 25, 1975

[21] Appl. No.: 616,717

[52] U.S. Cl. .................. 260/669 A; 260/674 SE
[51] Int. Cl.² .................................... C07C 15/00
[58] Field of Search ...................... 260/669 A

[56] References Cited
UNITED STATES PATENTS 3,684,665  8/1972  Hisao et al. .................. 260/669 A Primary Examiner—Delbert E. Gantz
Assistant Examiner—Joseph A. Boska

[57] ABSTRACT

A stream containing styrene and mixed xylenes, such as may be recovered from pyrolysis gasoline, is fractionated to obtain a stream containing ortho-xylene and styrene. Styrene is separated from the latter stream by an extraction process which employs succinonitrile as the solvent. Styrene is selectively absorbed by the succinonitrile, and is subsequently recovered from the resulting extract phase.

12 Claims, 1 Drawing Figure

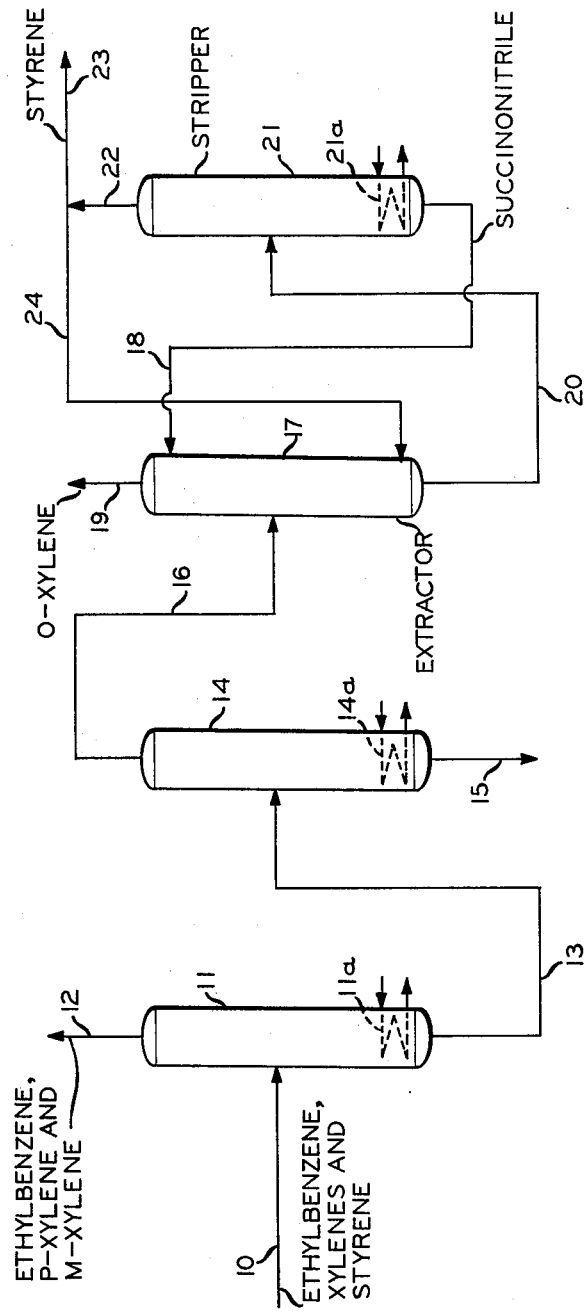

SEPARATION OF STYRENE FROM XYLENES

Pyrolysis gasoline from naphtha or gas-oil crackers often contains a relatively high concentration of styrene in the $C_8$ fraction. It is impractical to separate styrene from ortho-xylene by conventional fractionation because of the close boiling points (145.1° and 144.4° C., respectively). In accordance with this invention, it has been found that styrene can be separated from ortho-xylene by the use of succinonitrile as a selective solvent. The separation can be accomplished by liquid-liquid extraction or by extractive distillation. Liquid-liquid extraction is generally preferred in order to be able to operate at a lower temperature so as to minimize styrene polymerization. The invention is applicable to the purification of a $C_8$ fraction which also contains ethyl benzene, para-xylene and meta-xylene. These materials can be removed by fractionation before the extraction step.

The accompanying drawing is a schematic representation of apparatus which can be employed to carry out this invention.

Referring now to the drawing in detail, a feed stream containing ethyl benzene, xylenes and styrene is introduced through a conduit 10 which communicates with a first fractionator 11. The feed stream can also contain small amounts of $C_8$ and $C_9$ nonaromatics and heavy aromatics. Fractionator 11 is provided with a reboiler 11a. An overhead stream containing ethyl benzene, para-xylene, meta-xylene and any $C_8$ and $C_9$ nonaromatics is removed through a conduit 12. The kettle product stream removed through a conduit 13 comprises orthoxylene, styrene and any heavy aromatics. This kettle product is introduced into a second fractionator 14 which is provided with a reboiler 14a. A kettle product stream is removed from fractinator 14 through a conduit 15. This stream comprises any heavy aromatics present in the feed. The overhead stream from fractionator 14 is removed through a conduit 16 and introduced into an extractor 17.

A selective solvent is introduced into the upper region of extractor 17 by a conduit 18. A raffinate stream is removed from extractor 17 through a conduit 19. This raffinate stream comprises primarily ortho-xylene. An extract phase of solvent and styrene is removed from the bottom of extractor 17 through a conduit 20 and directed to a stripper 21 which is provided with a heater 21a. A styrene stream is removed from the top of stripper 21 through a conduit 22. A portion of this stream is recovered as product through a conduit 23, and the remainder is returned through a conduit 24 to the lower region of extractor 17 as reflux. The stripped solvent is removed from the bottom of stripper 21 through conduit 18 and passed to extractor 17.

In accordance with this invention, the solvent introduced into extractor 17 through conduit 18 comprises succinonitrile. In view of the fact that succinonitrile has a relatively high boiling point (266°C.), it is advantageous to add a small amount of water to the succinonitrile in order to facilitate stripping of the extracted styrene at relatively low temperatures. About 0.5 to 3.0 weight percent water in the succinonitrile is generally preferred, although larger amounts up to about 10 percent can be employed. Extractor 17 can be operated at any convenient temperature and pressure, but a temperature below about 65°C. is generally preferred in order to minimize polymerization of styrene. Stripping of the solvent extract stream in stripper 21 is preferably carried out under vacuum in order to keep the stripper temperature relatively low. A stripper pressure below about 50 mm Hg absolute (6.7 kPa), such as 40 to 50 mm Hg absolute (5.3–6.7 kPa) is preferred, although lower pressures such as 10 mm Hg (1.3 kPa) may be employed. As previously mentioned, column 17 can be an extractive distillation column. However, liquid-liquid extraction is preferred in order to be able to operate at lower temperatures.

The operability of this invention has been demonstrated by equilibrium data for a styrene, ortho-xylene, succinonitrile liquid-liquid system at 60°C. A mixture was formed of 49.67 weight percent ortho-xylene and 50.33 weight percent styrene. Succinonitrile containing 2.1 percent by weight water was added to the mixture in a weight ratio of 2.7:1. The resulting system was mixed and allowed to settle to form two phases. The hydrocarbon in the upper phase comprised 53.57% ortho-xylene and 46.43% styrene, by weight. The hydrocarbon in the lower phase comprised 46.80% ortho-xylene and 53.20% stylene, by weight. The upper phase contained 14.65% succinontrile, and the lower phase contained 83.4% succinonitrile. The selectively is thus equal to $$\frac{53.20}{46.80} \times \frac{53.57}{46.43}$$

or 1.312. Based on this selectivity, liquid-liquid extraction in a 67 tray extractor using a solvent to feed ratio of 22.1:1 and a reflux to product ratio of 14:1 both on a weight basis, will provide approximately 99% styrene recovery at 99% purity from a feed mixture of 65% ortho-xylene and 35% styrene.

A typical example of this invention involves the separation of a $C_8$ fraction of a pyrolysis gasoline. The calculated material balance of such a separation (kg/100 kg feed), based on the operating conditions described below, is as follows:

| Component | Conduit 10 | 12 | 13 | 16 | 15 | 19 | 23 |
|---|---|---|---|---|---|---|---|
| $C_8$ and $C_9$ Non-aromatics | 2.0 | 2.0 | | | | | |
| Ethylbenzene | 9.0 | 9.0 | | | | | |
| p-Xylene | 12.3 | 12.3 | | | | | |
| m-Xylene | 25.6 | 25.5 | 0.1 | 0.1 | | 0.1 | |
| o-Xylene | 14.1 | 0.1 | 14.0 | 14.0 | | 13.7 | 0.3 |
| Styrene | 35.0 | 0.1 | 34.9 | 34.8 | 0.1 | 0.3 | 34.5 |
| Heavy Aromatics | 2.0 | | 2.0 | | 2.0 | | |

Extractor 17 contains 67 trays, and is operated at 60°C. The solvent is succinonitrile containing 2.1% by weight water. The weight ratio of solvent to feed to extractor 17 is 22.1:1; and the weight ratio of relux (conduit 24) to product (conduit 23) is 14:1.

While this invention has been described in conjunction with presently preferred embodiments, it obviously is not limited thereto.

What is claimed is:

1. The method of separating styrene from a mixture comprising styrene, ethylbenzene, para-xylene, ortho-xylene and meta-xylene, which comprises fractionating the mixture to obtain a stream which consists essentially of ortho-xylene and styrene; introducing said stream consisting essentially of ortho-xylene and styrene into an intermediate region of a liquid-liquid extraction column; introducing a stream of succinonitrile into an upper region of said column; removing a raffinate stream enriched in ortho-xylene from the upper region of said column; removing an extract stream of succinonitrile enriched in styrene from the lower region of said column; and separating styrene from said extract stream.

2. The method of claim 1 wherein said mixture also contains $C_8$ and $C_9$ non-aromatics and aromatics heavier than $C_8$, and wherein the fractionation comprises introducing said mixture into a first fractionation column; operating said first column to obtain a first overhead stream comprising non-aromatics, ethylbenzene, para-xylene and meta-xylene and a first kettle stream comprising ortho-xylene, styrene and heavy aromatics; introducing said first kettle stream into a second fractionation column; and operating said second fractionation column to obtain a second kettle stream comprising heavy aromatics and a second overhead stream consisting essentially of ortho-xylene and styrene, said second overhead stream being the stream introduced into said extraction column.

3. The method of claim 1 wherein the extraction column is operated at a temperature below about 65° C.

4. The method of separating styrene from a mixture comprising styrene and ortho-xylene; which method comprises contacting said mixture with succinonitrile to form two phases, the first of which is rich in succinonitrile and styrene, and the second of which is rich in ortho-xylene; separating the first and second phases; and recovering styrene from the separated first phase.

5. The method of claim 4 wherein the mixture is contacted with succinonitrile containing water in a concentration of less than about 10 percent by weight.

6. The method of claim 4 wherein the water concentration is in the range of about 0.5 to 3 percent by weight.

7. The method of claim 4 wherein the contacting is conducted at a temperature below about 65° C.

8. The method of claim 4 wherein styrene is recovered from the first phase by heating said first phase.

9. The method of claim 8 wherein the heating is conducted at a pressure below about 6.7 kPa.

10. The method of separating styrene from a mixture comprising styrene and ortho-xylene; which method comprises introducing a stream of the mixture into an intermediate region of a liquid-liquid extraction column; introducing a stream of succinonitrile into an upper region of said column; removing a raffinate stream of ortho-xylene from the upper region of said column; removing an extract stream of succinonitrile and styrene from the lower region of said column; and separating styrene from said extract stream.

11. The method of claim 10 wherein said extract stream is introduced into a stripping column; heat is supplied to said stripping column; a stream of succinonitrile is removed from the lower region of said stripping column and returned to said extraction column; a stream of styrene is removed from the upper region of said stripping column; and a portion of said stream of styrene is introduced into the lower region of said extraction column.

12. The method of claim 10 wherein the extraction column is operated at a temperature below about 65° C.

* * * * *